(12) United States Patent
Wang et al.

(10) Patent No.: US 8,658,789 B2
(45) Date of Patent: Feb. 25, 2014

(54) METHOD FOR PREPARING LINEZOLID AND INTERMEDIATES THEREOF

(75) Inventors: Ping Wang, Zhejiang Province (CN); Qiangbiao Pan, Zhejiang Province (CN); Yangzhou Li, Zhejiang Province (CN); Daoliang Zheng, Zhejiang Province (CN)

(73) Assignee: Lianhe Chemical Technology Co., Ltd., Taizhou (CN)

( * ) Notice: Subject to any disclaimer, the term of this patent is extended or adjusted under 35 U.S.C. 154(b) by 218 days.

(21) Appl. No.: 13/144,242

(22) PCT Filed: Jan. 8, 2010

(86) PCT No.: PCT/CN2010/070090
§ 371 (c)(1),
(2), (4) Date: Jul. 12, 2011

(87) PCT Pub. No.: WO2010/081404
PCT Pub. Date: Jul. 22, 2010

(65) Prior Publication Data
US 2011/0275805 A1    Nov. 10, 2011

(30) Foreign Application Priority Data
Jan. 13, 2009 (CN) .......................... 2009 1 0045209

(51) Int. Cl.
C07D 413/10 (2006.01)
C07C 211/01 (2006.01)

(52) U.S. Cl.
USPC .......................................... 544/137; 564/391

(58) Field of Classification Search
None
See application file for complete search history.

(56) References Cited

U.S. PATENT DOCUMENTS

2007/0032472 A1   2/2007   Rao et al.

FOREIGN PATENT DOCUMENTS

| CN | 1673224 A | 9/2005 |
|---|---|---|
| CN | 1772750 A | 5/2006 |
| JP | A-2003-206282 | 7/2003 |
| WO | WO 95/07271 A1 | 3/1995 |
| WO | WO 99/24393 A1 | 5/1999 |
| WO | WO 2006/008754 A1 | 1/2006 |
| WO | WO 2007/116284 A1 | 10/2007 |

OTHER PUBLICATIONS

Lohray et al. Tetrahedron Lett. 1999, 4855-4866.*
Yu et al. Bioorganic & Medicinal Chemistry Letters 12 (2002) 857-859.*
Greene et al. Greene's Protective Groups in Organic Synthesis, Fourth Edition, John Wiley & Sons, Inc 2007 pp. 814-817, 828-829.*
Mallesham et al., "Highly Efficient CuI-Catalyzed Coupling of Aryl Bromides with Oxazolidinones Using Buchwald's Protocol: A Short Route to Linezolid and Toloxatone," Organic Letters, vol. 5, No. 7, 2003, pp. 963-965.
International Search Report issued in International Patent Application No. PCT/CN2010/070090 dated Apr. 1, 2010 (with translation).
Written Opinion issued in International Patent Application No. PCT/CN2010/070090 dated Apr. 1, 2010 (with translation).
Chinese Office Action issued in Chinese Patent Application No. 200910045209.9 dated May 17, 2011 (with translation).

* cited by examiner

Primary Examiner — Yong Chu
Assistant Examiner — Ana Z Muresan
(74) Attorney, Agent, or Firm — Oliff PLC

(57) ABSTRACT

A method for preparing the linezolid (compound 1), which comprises the steps of: (1) carrying out the debenzyl reaction of compound 4 in solvent, to obtain the compound 5 or its acetic acid salt; (2) carrying out the acetylation reaction in the amino of the compound 5 or its acetic acid salt obtained in step (1) in solvent to obtain the compound 1. The intermediates to prepare the compound 1 and the acetic acid salt of compound 5. The present preparation method is easy to obtain the chiral materials and the chiral materials are cheap, the process and the post treatment are simple, the intermediate products and the end product are easy to be purified, the total yield is high, their purities are also high, this preparation method is easy to be used in the industry manufacture.

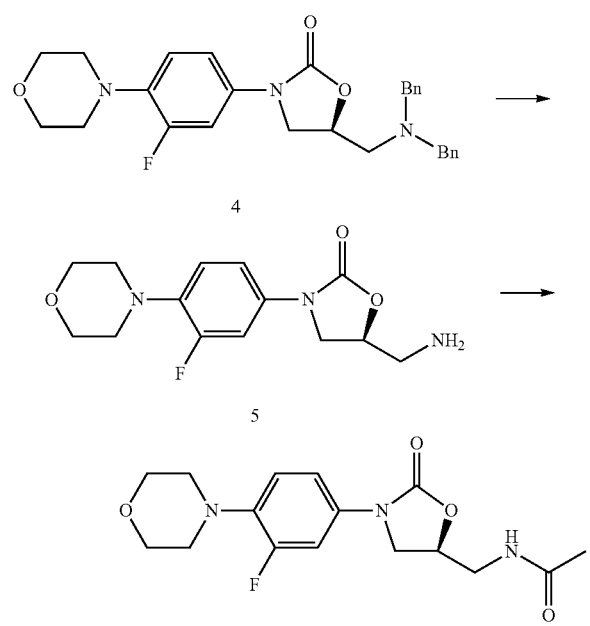

10 Claims, No Drawings

METHOD FOR PREPARING LINEZOLID AND INTERMEDIATES THEREOF

FIELD OF THE INVENTION

The present invention relates to a method for preparing a medicine and the intermediates thereof. Particularly, the present invention relates to a method for preparing linezolid and the intermediates thereof.

BACKGROUND OF THE INVENTION

Linezolid, the English name of which is Linezolid and the chemical name is (S)—N-{[3-(3-fluoro-4-(4-morpholinophenyl)-2-oxooxazolidin-5-yl]methyl}acetamide, and the structural formula is as below:

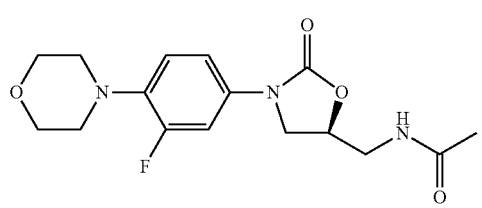

Linezolid is the first synthetic antibiotic belonging to the class of oxazolidinone, and it was researched and developed by the US Pharmacia & Upjhon Corporation and was approved by FDA for marketing on Apr. 18, 2004. The medicine can be used to treat hospital-acquired pneumonia, infection of the skin and soft tissues and community-acquired pneumonia, and the curative effect has been proved by clinical practice. Besides, the clinical curative effect of linezolid is superior or equal to that of conventional antibacterial, and it is also effective on infection of methicillin-resistant *Staphylococcus aureus* (MRSA), glycopeptides-resistant *enterococcus* and penicillin-resistant *Streptococcus pneumonia* (PRSP). Linezolid is low-toxic, safe and simple to use. Linezolid is a bacterial protein synthesis inhibitor, and it is different from other pharmaceuticals in that it has no effect on the activity of peptidyl-transferase but to combine with the 50S subunit ribosome alternatively. Since the action site and style of linezolid is unique, cross-resistance between linezolid and other bacterial protein synthesis inhibitor will not happen and it is not likely to induce drug resistance in vitro.

At present, several main synthetic routes of linezolid are as follows:
1. WO9507271

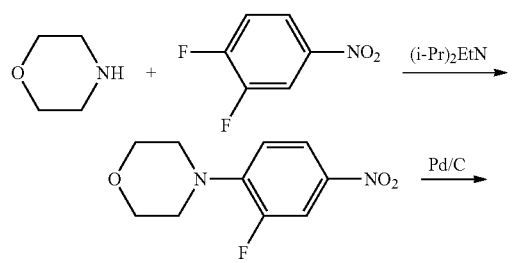

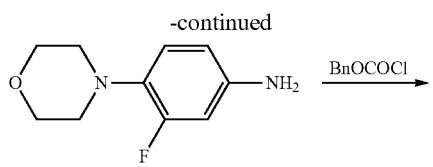

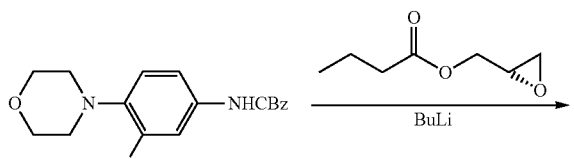

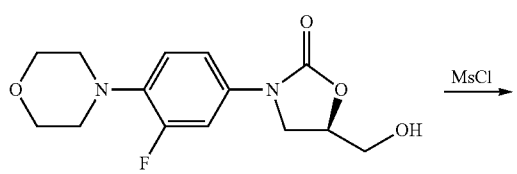

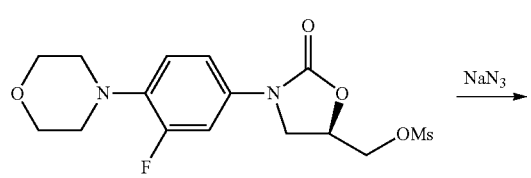

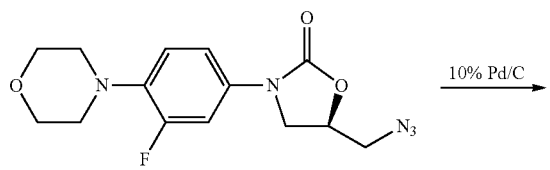

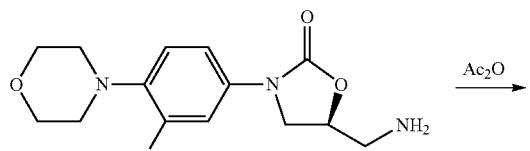

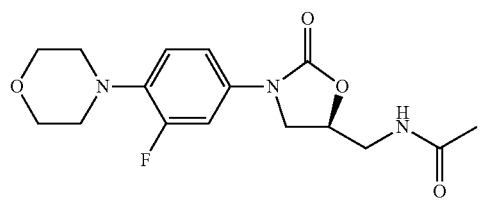

In the cyclization reaction of this route, harsh reaction conditions of low temperature of −78° C. and protection of inert gas etc. are indispensable, which is disadvantageous to industrial manufacture. Moreover, the usage of sodium azide and high-pressure catalytic hydrogenation has high requirement of synthetic equipment and has some potential safety hazards.

2. WO9924393
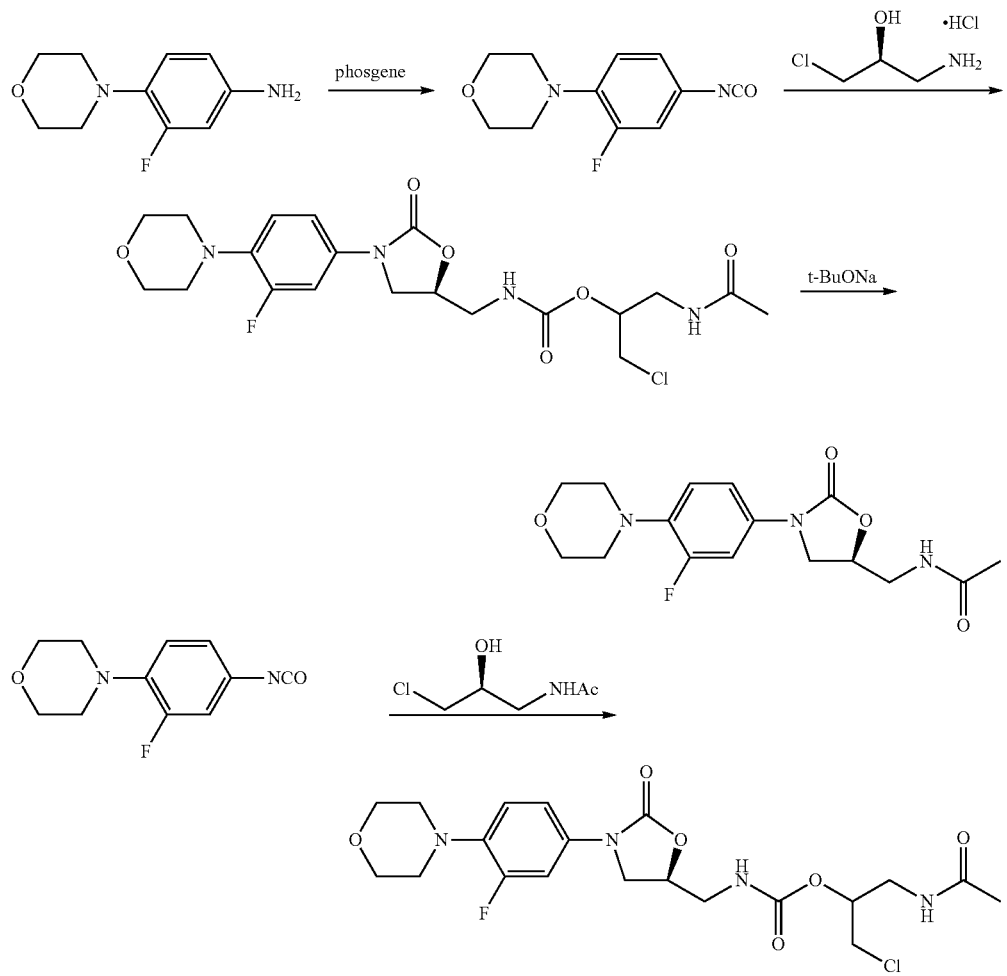
Highly toxic phosgene is used in the route and the intermediate of the second step has to be distilled under high vacuum. The product is easy to decompose when heated and the yield is low. So it is not suitable for industrial manufacture.
3. CN1673224
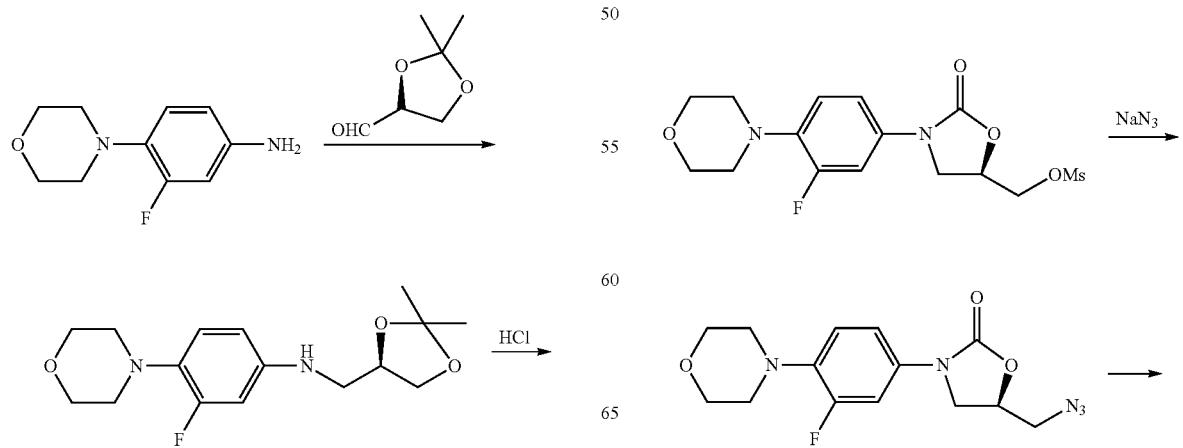

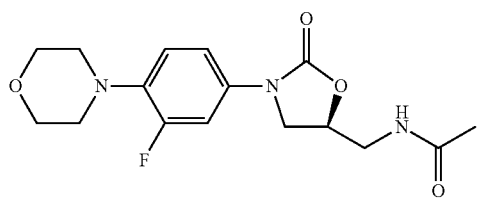 [SMILES: CC(=O)NC[C@H]1CN(c2ccc(N3CCOCC3)c(F)c2)C(=O)O1]

The yield of the cyclization reaction of this route is low and sodium azide and high-pressure catalytic hydrogenation are also used to introduce amino group which is not suitable for industrial manufacture.

4. US2007032472

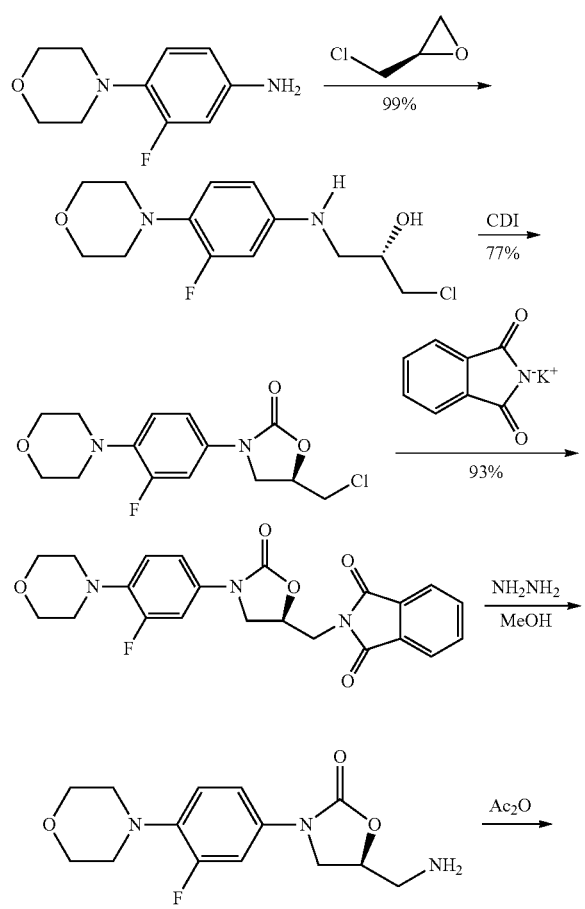

The yield of the first step cannot be repeated. The starting materials can not convert completely and the ratio of the product to the isomer is about 85:15 and the by-product is difficult to separate.

5. CN1772750

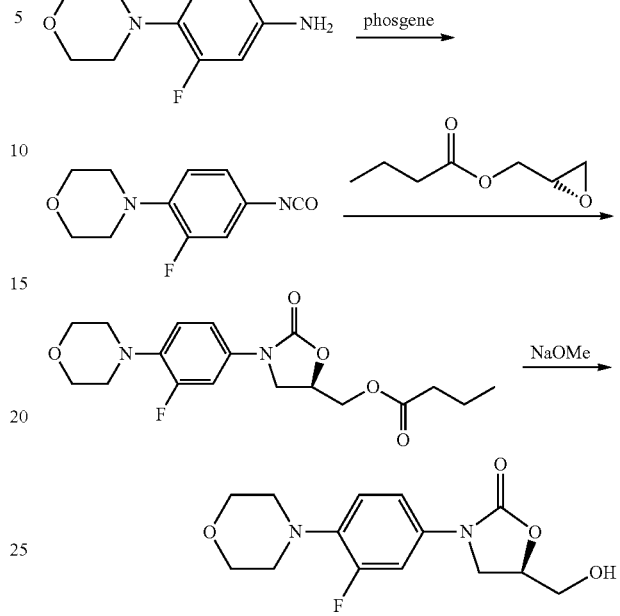

Highly toxic phosgene and high vacuum distillation are used in this route. In the following reactions, sodium azide and high-pressure catalytic hydrogenation are also required.

6. WO2007116284

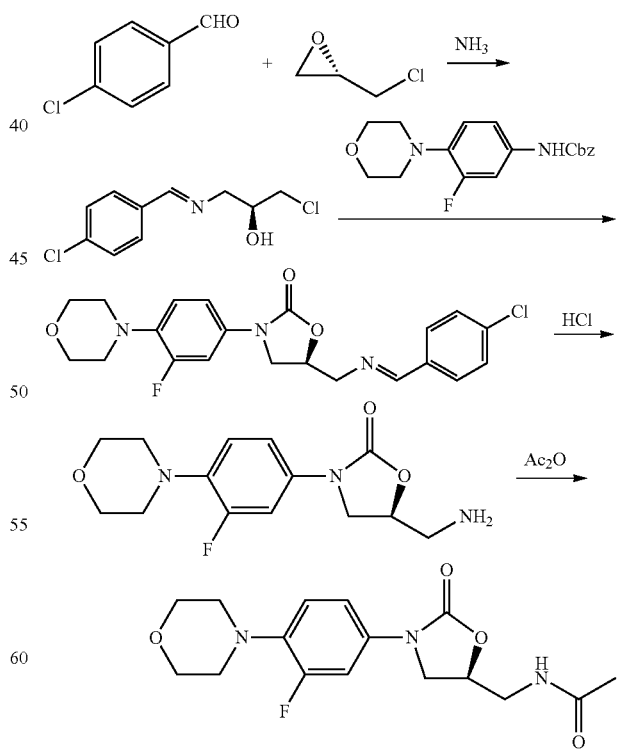

The yields of the first three steps are low and this route brings much pressure on the reduction of the cost.

7. Organic Letters, 2003, 5, 963

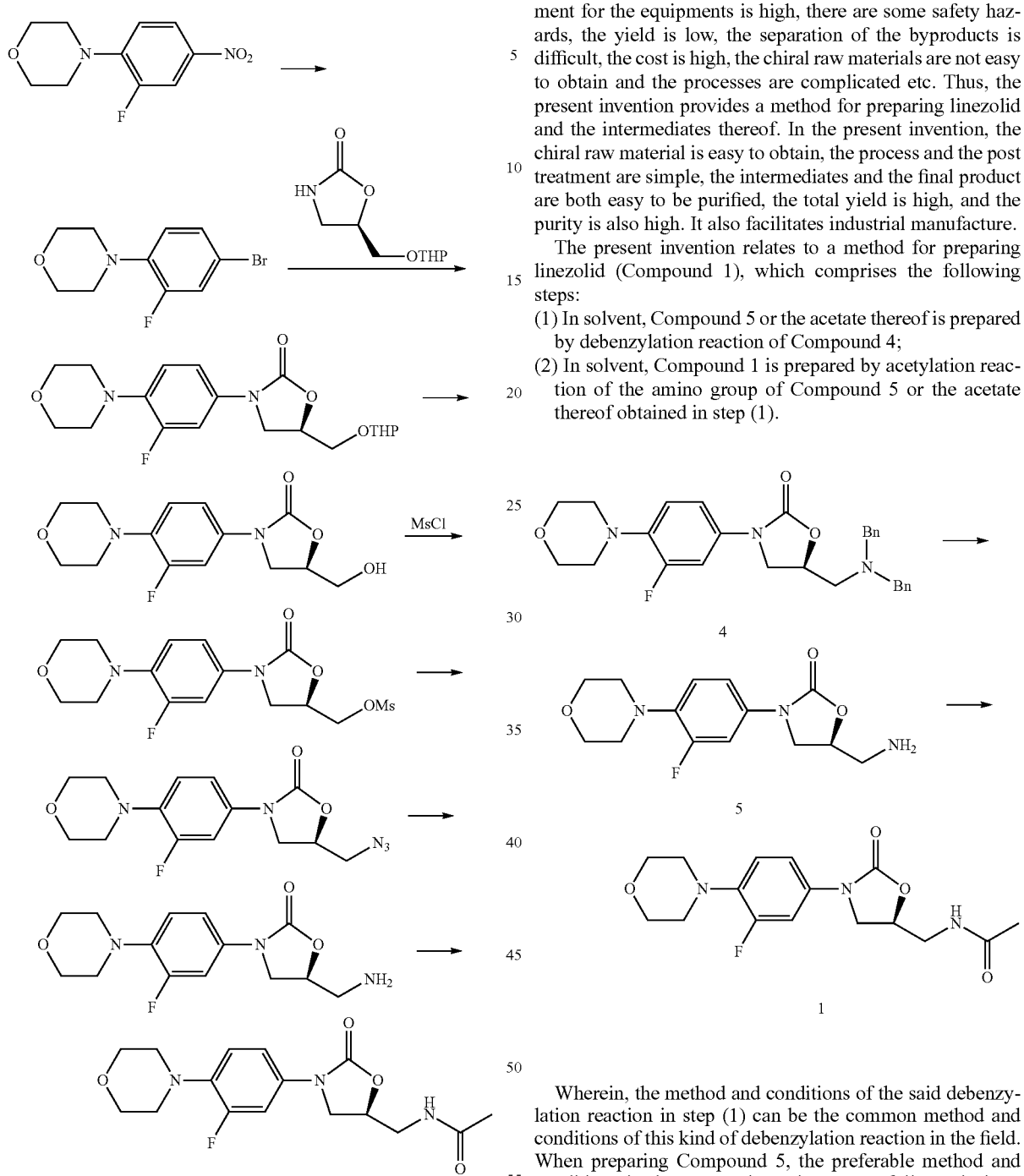

The yield of the coupling reaction is not high in this route. The synthesis of the chiral materials is complicated and sodium azide and high-pressure catalytic hydrogenation are also required. Comparing the seven routes above, there are some limitations such as the use of sodium azide and high-pressure catalytic hydrogenation etc., which bring about some difficulties to the industrial manufacture of linezolid.

SUMMARY OF INVENTION

The technical problem to be solved by the invention is to overcome the disadvantages in the present preparation method of linezolid in which the operation conditions are harsh and not suitable for industrial manufacture, the requirement for the equipments is high, there are some safety hazards, the yield is low, the separation of the byproducts is difficult, the cost is high, the chiral raw materials are not easy to obtain and the processes are complicated etc. Thus, the present invention provides a method for preparing linezolid and the intermediates thereof. In the present invention, the chiral raw material is easy to obtain, the process and the post treatment are simple, the intermediates and the final product are both easy to be purified, the total yield is high, and the purity is also high. It also facilitates industrial manufacture.

The present invention relates to a method for preparing linezolid (Compound 1), which comprises the following steps:

(1) In solvent, Compound 5 or the acetate thereof is prepared by debenzylation reaction of Compound 4;
(2) In solvent, Compound 1 is prepared by acetylation reaction of the amino group of Compound 5 or the acetate thereof obtained in step (1).

Wherein, the method and conditions of the said debenzylation reaction in step (1) can be the common method and conditions of this kind of debenzylation reaction in the field. When preparing Compound 5, the preferable method and conditions in the present invention are as follows: in inert organic solvent, Compound 4 is debenzylated to yield Compound 5 in presence of the catalyst and hydrogen source.

Wherein, the said catalyst is preferably Pd—C and/or Pt—C; more preferably, Pd—C; the dosage of the said catalyst is preferably 0.01~0.5 times of the molar quantity of Compound 4, more preferably, 0.01~0.2 times of the molar quantity of Compound 4; the said hydrogen source is preferably one or more selected from the group consisting of hydrogen, hydrazine hydrate, ammonium formate, formic acid and formic acid-triethylamine azeotrope, most preferably hydrogen; the dosage of the said hydrogen source is preferably more than one time of the molar quantity of Compound 4, the more the better; the said inert organic solvent is preferably one or more selected from the group consisting of lower alcohol, ketone solvent, ester solvent, aromatic hydrocarbon and ether, more preferably ester solvent; the said lower alcohol is preferably one or more selected from the group consisting of methanol, ethanol, propanol isopropanol and butanol; the said ester solvent is preferably ethyl acetate and/or n-butyl acetate; the said ketone solvent is preferably acetone; the dosage of the said inert organic solvent is preferably 1~100 times of the molar quantity of Compound 4, more preferably 8~20 times; the said reaction temperature is preferably 0° C.~50° C., more preferably 15° C.~30° C.; the said reaction pressure is preferably 1~50 atm, more preferably 1~5 atm; the said reaction time is preferably detected until the end of the reaction, more preferably detected by TLC until the complete consumption of the reactants.

In step (1), when preparing the acetate of Compound 5, it can be prepared directly by forming salt from Compound 5 and acetic acid according to normal operations. The preferable method and condition in the present invention is that in organic solvent, Compound 4 is debenzylated in presence of catalyst and hydrogen source, and after the reaction, a salt is formed by the obtained Compound 5 with acetic acid.

Wherein, the said catalyst is preferably one or more selected from the group consisting of Pd—C, Pt—C, boron tribromide and boron trifluoride, more preferably Pd—C; The molar ratio of the said catalyst to Compound 4 is preferably 0.005~0.5, more preferably 0.01~0.2; the said hydrogen source is preferably one or more selected from the group consisting of hydrogen, hydrazine hydrate, ammonium formate, formic acid and triethylamine-formic acid azeotrope, most preferably hydrogen; the dosage of the said hydrogen source is preferably more than one time of the molar quantity of Compound 4, the more the better; the said organic solvent is preferably one or more selected from the group consisting of water, ethyl acetate, ethanol, toluene, dioxane and methylene dichloride, more preferably ethyl acetate; the ratio of the volume of the solvent to the mass of Compound 4 is preferably 1~200 ml/g; the said reaction time is preferably detected until the end of the reaction, generally 1~96 hours; the said reaction temperature is preferably 0~100° C., more preferably 10~60° C.

In step (2), when preparing Compound 1 from Compound 5, the method and conditions of the said acetylation reaction of the amino group can be the common method and conditions of this kind of acetylation reaction in the field. For instance, Compound 1 can be obtained via the reaction of Compound 5 with acetyl chloride or acetic anhydride. The present invention can refer to the methods and conditions in Patent WO 9507271 to obtain Compound 1.

In step (2), when preparing Compound 1 from the acetate of Compound 5, the method and conditions of the said acetylation reaction of the amino group can be the common method and conditions of this kind of acetylation reaction in the field. For instance, Compound 1 can be obtained via the reaction of the acetate of Compound 5 with acetyl chloride or acetic anhydride, more preferably acetic anhydride. The present invention can refer to the methods and conditions in Patent WO 9507271 to obtain Compound 1.

In the present invention, the said Compound 4 can be synthesized by the following method: in solvent, a cyclization reaction of Compound 2 and Compound 3 is performed.

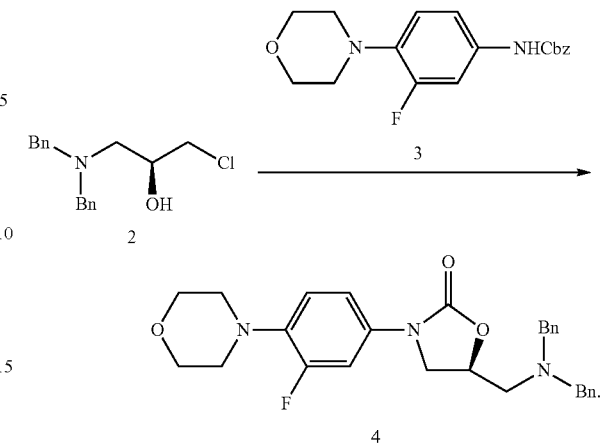

Wherein, the method and conditions of the said cyclization reaction can be the common method and conditions of this kind of cyclization reaction in the field. The methods and conditions particularly preferred in the present invention are described below: in inert organic solvent, Compound 4 is prepared by the cyclization reaction of Compound 2 and Compound 3 in presence of alkali.

Wherein, the dosage of the said Compound 2 is preferably 1~10 times of the molar quantity of Compound 3, more preferably 1~3 times; the said alkali is preferably one or more selected from the group consisting of n-butyl lithium, tert-butyl lithium. lithium hydroxide and lithium tert-butoxide, more preferably lithium tert-butoxide and/or n-butyl lithium; the dosage of the said alkali is preferably 1~10 times of the molar quantity of Compound 2, more preferably 2~6 times; the said inert organic solvent is preferably one or more selected from the group consisting of lower alcohol, ketone, aromatic hydrocarbon, ether, haloalkane, N,N-dimethyl formamide, N,N-dimethyl acetamide, dimethyl sulfoxide and acetonitrile; the said reaction temperature is preferably −78° C.~100° C., more preferably −78° C.~50° C.; The said reaction time is preferably detected until the end of reaction, such as detected by TLC until the complete consumption of the reactants.

Wherein, the said Compound 3 can be synthesized conveniently with reference to a patent, of which the application number is WO 9507271.

In the present invention, the said Compound 2 can be synthesized by the following method: in solvent or in the condition without solvent, a nucleophilic ring opening reaction is performed by (S)-epichlorohydrin and dibenzyl amine.

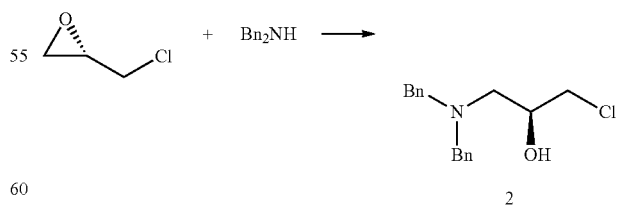

Wherein, the method and conditions of the said nucleophilic ring opening reaction can be the common method and conditions of this kind of nucleophilic ring opening reaction in the field. The methods and conditions particularly preferred in the present invention are described below: in inert organic solvent or in the condition without solvent, Compound 2 is prepared by the nucleophilic ring opening reaction of (S)-epichlorohydrin and dibenzyl amine in presence of Lewis acid.

Wherein, the said Lewis acid, the function of which is to accelerate the reaction and increase the reaction yield, is preferably one or more selected from the group consisting of lithium chloride, lithium bromide, calcium chloride, lithium hydroxide, zinc chloride, stannic chloride and ferric chloride, more preferably one or more selected from the group consisting of lithium chloride, lithium bromide and calcium chloride, most preferably lithium bromide and/or calcium chloride; The dosage of said Lewis acid is preferably 0.01~3 times of the molar quantity of dibenzyl amine, more preferably 0.1~1 times; the dosage of (S)-epichlorohydrin is preferably more than 1 time of the molar quantity of dibenzyl amine, the more the better; or (S)-epichlorohydrin can be used as the reaction medium directly without solvent; the said inert organic solvent is preferably one or more selected from the group consisting of lower alcohol, ketone, ester, aromatic hydrocarbon, ether, haloalkane, N,N-dimethyl formamide, N,N-dimethyl acetamide, dimethyl sulfoxide and acetonitrile; wherein the said lower alcohol is preferably one or more selected from the group consisting of methanol, ethanol, propanol, isopropanol and butanol; the said ketone is preferably acetone; the said ester is preferably selected from ethyl acetate and/or isopropyl acetate; the said aromatic hydrocarbon is preferably selected from toluene and/or xylene; the said ether is preferably one or more selected from the group consisting of tetrahydrofuran, ethylene glycol dimethyl ether and isopropyl ether; the said haloalkane is preferably one or more selected from the group consisting of methylene dichloride, chloroform and 1,2-dichloroethane; the dosage of the said inert organic solvent is preferably 1~100 times of the amount of dibenzyl amine, more preferably 8~10 times; the preferred reaction temperature is 0° C.~120° C., more preferably 20° C.~80° C.; the preferred reaction time is detected until the end of reaction, such as detected by TLC until the complete consumption of reactants.

In the preparation method of the present invention, the optimal conditions in the above processing steps can be combined optionally to get the preferable examples of the invention. In the preparation method of the present invention, after the completion of the reaction the pure product can be obtained in high yield just by simple post treatments, such as drying, filtration, concentration, crystallization etc.

This invention also relates to an intermediate Compound 4 which is used to prepare Compounds 1:

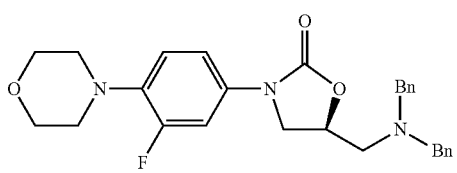

4

This invention also relates to an intermediate Compound 2 which is used to prepare Compounds 1:

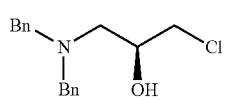

2

This invention also relates to the acetate of Compound 5:

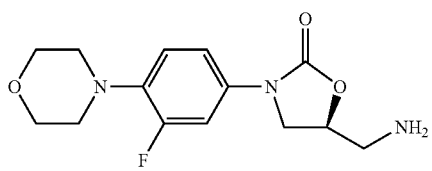

5

The acetate of Compound 5 is in high purity, easy to separate, and not liable to deliquesce. Moreover, the next step to prepare Compound 1 is the acetylation reaction and no new impurities will be introduced into the final product.

In this invention, the said "lower alcohol" means alcohol with the carbon chain length of $C_1$~$C_4$.

In this invention, Bn means benzyl; Cbz means carbobenzoxy.

Unless otherwise stated, the raw materials and reagents used in the present invention are all commercially available.

The active and progressive effects of the present invention are that the chiral raw materials are available easily and cheap in the preparation method, the process is simple, the cost is low, the post treatment is simple, the intermediate and the end product are easily purified, the total yield is high, and the purity is also high. This method is not only suitable for a small-scale laboratory preparation but also suitable for a large-scale industrial manufacture.

EXAMPLES

The following examples are used to further explain this invention, but not to restrict the scope of this invention.

In this invention, the said ambient temperature means 20° C.~40° C.; the normal pressure means 0.8 atm~1.2 atm. Unless otherwise stated, all the examples below are carried out under normal pressure.

Example 1

Preparation of 3-fluoro-4-morpholinyl nitrobenzene 3,4-difluoro-nitrobenzene (100 g, 0.63 mol) was added dropwise to morpholine (60 g, 0.69 mol) and triethylamine (70 g, 0.69 mol) in ethyl acetate (300 mL) within 1 hour while maintaining the temperature below 50° C. The mixture is stirred at 45~50° C. for 10 hours until the completion of the reaction. The mixture was extracted with ethyl acetate, washed with brine and dried over anhydrous magnesium sulfate, filtered, dried, to provide 138 g of yellow solid in 97% yield.

$^1$H NMR (300 MHz, CDCl$_3$) δ: 3.28 (m, 4H, CH$_2$CH$_2$N), 3.88 (m, 4H, CH$_2$CH$_2$O), 6.92 (t, 1H, ArH), 7.91 (dd, 1H, ArH), 7.99 (dd, 1H, ArH)

HPLC: 99.1%.

Example 2

Preparation of 3-fluoro-4-morpholinyl aniline

10% Pd—C 4.0 g was added to 3-fluoro-4-morpholinyl nitrobenzene (40 g, 177 mmol), ammonium formate (50 g, 793 mmol) in 200 mL of ethyl acetate and stirred at 45~50° C. for 8 h until the completion of the reaction. The mixture was then filtrated and separated by water. The organic layer was washed with brine and dried over anhydrous magnesium sulfate, filtered, and the solvent was evaporated to provide 33 g of solid in 95% yield.

$^1$H NMR (300 MHz, CDCl$_3$) δ: 3.01 (m, 4H, CH$_2$CH$_2$N), 3.56 (br, 2H, ArNH$_2$) 3.86 (m, 4H, CH$_2$CH$_2$O), 6.41 (m, 2H, ArH), 6.79 (m, 1H, ArH)
HPLC: 99.0%.

Example 3

Preparation of N-carbobenzoxy-4-morpholinyl aniline (Compound 3)

Sodium bicarbonate (17 g, 202 mmol) and 150 mL water were added to a solution of 3-fluoro-4-morpholinyl aniline (26 g, 133 mmol) of acetone (200 mL). The reaction mixture was cooled to −10~0° C. Carbobenzoxy chloride (26 g. 152 mmol) was added dropwise within 1 hour. The mixture raised to room temperature (25° C.) naturally, and stirred at this temperature for 2 hours. Then the material liquid was poured into 500 mL ice water, filtered, and dried to provide 39 g of off-white solid in 90% yield.
$^1$H NMR (300 MHz, CDCl$_3$) δ: 3.01 (m, 4H, CH$_2$CH$_2$N), ArNH$_2$ 3.85 (m, 4H, CH$_2$CH$_2$O), 5.14 (s, 2H, ArCH$_2$) 6.93 (m, 3H, ArH), 7.35 (m, 6H, ArH, CNHC)
HPLC: 98.2%, 37.6 g white solid was obtained after recrystallization with ethyl acetate, HPLC: 99.4%.

Example 4

Preparation of (S)-1-chloro-3-(dibenzylamino)propan-2-ol (Compound 2)

Dibenzylamine (39.4 g, 0.20 mol) was added to 100 mL of methylene dichloride and stirred for 30 minutes. (S)-epichlorohydrin (21 g, 0.23 mol) was then added. The mixture was stirred at room temperature (25° C.) for 20 hours. Filtered, and the solvent was evaporated to provide 55 g of colorless oil in 93% yield.
$^1$H NMR (300 MHz, CDCl$_3$) δ: 2.63 (m, 2H, CH$_2$N), 3.25 (s, 1H, CHOH), 3.47 (q, 2H, CH$_2$Cl), 3.53 (d, 2H, ArCH$_2$N), 3.79 (d, 2H, ArCH$_2$N), 3.90 (m, 1H, CHOH), 7.27-7.36 (m, 10H, ArH).
HPLC: 98.4%.

Example 5

Preparation of (S)-1-chloro-3-(dibenzylamino)propan-2-ol (Compound 2)

Dibenzylamine (39.4 g, 0.20 mol) and calcium chloride (1 g, 9 mmol) were added to 100 mL of methylene dichloride and stirred for 30 minutes. (S)-epichlorohydrin (21 g, 0.23 mol) was then added. The mixture was stirred at room temperature (30° C.) for 5 hours. Filtered, and the solvent was evaporated to provide 56 g of colorless oil in 95% yield.
$^1$H NMR (300 MHz, CDCl$_3$) δ: 2.63 (m, 2H, CH$_2$N), 3.25 (s, 1H, CHOH), 3.47 (q, 2H, CH$_2$Cl), 3.53 (d, 2H, ArCH$_2$N), 3.79 (d, 2H, ArCH$_2$N), 3.90 (m, 1H, CHOH), 7.27-7.36 (m, 10H, ArH).
HPLC: 97.2%.

Example 6

Preparation of (S)-1-chloro-3-(dibenzylamino)propan-2-ol (Compound 2)

Dibenzylamine (39.4 g, 0.20 mol) and lithium bromide (1.7 g, 20 mmol) were added to 100 mL ethyl acetate and stirred for 30 minutes. (S)-epichlorohydrin (21 g, 0.23 mol) was then added. The reaction went on at room temperature (32° C.) for 2 hours. Filtered, and the solvent was evaporated to provide 53 g of colorless oil with 90% yield.
$^1$H NMR (300 MHz, CDCl$_3$) δ: 2.63 (m, 2H, CH$_2$N), 3.25 (s, 1H, CHOH), 3.47 (q, 2H, CH$_2$Cl), 3.53 (d, 2H, ArCH$_2$N), 3.79 (d, 2H, ArCH$_2$N), 3.90 (m, 1H, CHOH), 7.27-7.36 (m, 10H, ArH).
HPLC: 92.0%.

Example 7

Preparation of (S)-1-chloro-3-(dibenzylamino)propan-2-ol (Compound 2)

Dibenzylamine (39.4 g, 0.20 mol) and lithium bromide (1.7 g, 20 mmol) were added to (S)-epichlorohydrin (185 g, 2 mol). The mixture was stirred at room temperature (25° C.) for 2 hours, Filtered, and the solvent was evaporated to provide 53 g of colorless Oil in 90% yield.
$^1$H NMR (300 MHz, CDCl$_3$) δ: 2.63 (m, 2H, CH$_2$N), 3.25 (s, 1H, CHOH), 3.47 (q, 2H, CH$_2$Cl), 3.53 (d, 2H, ArCH$_2$N), 3.79 (d, 2H, ArCH$_2$N), 3.90 (m, 1H, CHOH), 7.27-7.36 (m, 10H, ArH).
HPLC: 90.2%.

Example 8

Preparation of (S)-1-chloro-3-(dibenzylamino)propan-2-ol (Compound 2)

Dibenzylamine (39.4 g, 0.20 mol) and calcium chloride (1 g, 9 mmol) were added to (S)-epichlorohydrin (185 g, 2 mol). The mixture was stirred at room temperature (33° C.) for 8 hours. Filtered, and the solvent was evaporated to provide 57 g of colorless oil in 97% yield.
$^1$H NMR (300 MHz, CDCl$_3$) δ: 2.63 (m, 2H, CH$_2$N), 3.25 (s, 1H, CHOH), 3.47 (q, 2H, CH$_2$Cl), 3.53 (d, 2H, ArCH$_2$N), 3.79 (d, 2H, ArCH$_2$N), 3.90 (m, 1H, CHOH), 7.27-7.36 (m, 10H, ArH).
HPLC: 98.2%.

Example 9

Preparation of (S)-5-(((dibenzylamino)methyl)-3-(3-fluoro-4-morpholinophenyl) oxazolidin-2-one (Compound 4)

N-carbobenzoxy-3-fluoro-4-morpholinylaniline (0.33 g, 1 mmol) was added under nitrogen atmosphere to 5 mL of DMF (N,N-dimethyl formamide), and mixture was cooled to −10~0° C. A solution of lithium tert-butoxide (2.5 mL, 2.5 mmol) in tetrahydrofuran was added dropwise. The mixture was warmed to room temperature (25° C.) naturally and stirred for 2 hours. (S)-1-chloro-3-(dibenzylamino)propan-2-ol (0.32 g, 1.1 mmol) was then added and the mixture was stirred at room temperature for 20 hours. Saturated ammonium chloride solution and ethyl acetate were added to separate. The organic layer was washed with water and dried over anhydrous magnesium sulfate, filtered, and the solvent was evaporated to provide 0.42 g of white solid in 88% yield.
$^1$H NMR (300 MHz, CDCl$_3$) δ: 2.83 (m, 2H, CHCH$_2$N), 3.06 (t, 4H, CH$_2$CH$_2$N), 3.42 (m, 1H, CH$_a$CHO), 3.64 (m, 4H, ArCH$_2$N), 3.69 (m, 1H, CH$_b$NO), 3.88 (t, 4H, CH$_2$CH$_2$N), 4.55 (m, 1H, CH$_2$CHO), 6.91 (m, 1H, ArH), 7.01 (m, 1H, ArH), 7.23-7.34 (m, 11H, ArH).
HPLC: 95.6%, 0.36 g white solid was provided after recrystallization with ethyl acetate, HPLC: 99.3%.

Example 10

Preparation of (S)-5-((dibenzylamino)methyl)-3-(3-fluoro-4-morpholinophenyl) oxazolidin-2-one (Compound 4)

N-carbobenzoxy-3-fluoro-4-morpholinylaniline (0.33 g, 1 mmol) and lithium tert-butoxide (0.19 g, 2.4 mmol) were added under nitrogen atmosphere to 10 mL of tetrahydrofuran and the mixture was stirred at room temperature for 2 hours. (S)-1-chloro-3-(dibenzylamino)propan-2-ol (0.32 g, 1.1 mmol) was added and then reaction mixture was heated to 60° C. and stirred for 8 hours. Saturated ammonium chloride solution, and ethyl acetate were added to separate. The organic layer was washed with water and dried over anhydrous magnesium sulfate, filtered, and the solvent was evaporated to provide 0.39 g of off-white solid in 82% yield.

$^1$H NMR (300 MHz, CDCl$_3$) δ: 2.83 (m, 2H, CHCH$_2$N), 3.06 (t, 4H, CH$_2$CH$_2$N), 3.42 (m, 1H, CH$_a$CHO), 3.64 (m, 4H, ArCH$_2$N), 3.69 (m, 1H, CH$_b$NO), 3.88 (t, 4H, CH$_2$CH$_2$N), 4.55 (m, 1H, CH$_2$CHO), 6.91 (m, 1H, ArH), 7.01 (m, 1H, ArH), 7.23-7.34 (m, 11H, ArH).

HPLC: 96.3%.

Example 11

Preparation of (S)-5-((dibenzylamino)methyl)-3-(3-fluoro-4-morpholinophenyl) oxazolidin-2-one (Compound 4)

N-carbobenzoxy-3-fluoro-4-morpholinyl aniline (0.33 g, 1 mmol) and lithium tert-butoxide (0.19 g, 2.4 mmol) were added under nitrogen atmosphere to 10 mL of methylene dichloride and the mixture was stirred at room temperature for 0.5 hours. (S)-1-chloro-3-(dibenzylamino) propan-2-ol (0.32 g, 1.1 mmol) was added and the reaction mixture was heated to reflux and stirred for 5 hours. Saturated ammonium chloride solution, and ethyl acetate were added to separate. The organic layer was washed with water and dried over anhydrous magnesium sulfate, filtered, and the solvent was evaporated to provide 0.33 g of off-white solid in 69% yield.

$^1$H NMR (300 MHz, CDCl$_3$) δ: 2.83 (m, 2H, CHCH$_2$N), 3.06 (t, 4H, CH$_2$CH$_2$N), 3.42 (m, 1H, CH$_a$CHO), 3.64 (m, 4H, ArCH$_2$N), 3.69 (m, 1H, CH$_b$NO), 3.88 (t, 4H, CH$_2$CH$_2$N), 4.55 (m, 1H, CH$_2$CHO), 6.91 (m, 1H, ArH), 7.01 (m, 1H, ArH), 7.23-7.34 (m, 11H, ArH).

HPLC: 97.2%.

Example 12

Preparation of (S)-5-((dibenzylamino)methyl)-3-(3-fluoro-4-morpholinophenyl)oxazolidin-2-one (Compound 4)

N-carbobenzoxy-3-fluoro-4-morpholinylaniline (0.33 g, 1 mmol) and lithium tert-butoxide (0.10 g, 1.3 mmol) were added under nitrogen atmosphere to 10 mL of tetrahydrofuran and the mixture was stirred at room temperature for 2 hours (Solution 1). (S)-1-chloro-3-(dibenzylamino)propan-2-ol (0.32 g, 1.1 mmol) and lithium tert-butoxide were added to 10 mL tetrahydrofuran and stirred at room temperature for 2 hours (Solution 2). Solution 2 was added to Solution 1 and the material liquid was heated to 50° C. and reacted for 5 hours. Saturated ammonium chloride solution, and ethyl acetate were added to separate. The organic layer was washed with water and dried over anhydrous magnesium sulfate, filtered, and the solvent was evaporated to provide 0.40 g of off-white solid in 84% yield.

$^1$H NMR (300 MHz, CDCl$_3$) δ: 2.83 (m, 2H, CHCH$_2$N), 3.06 (t, 4H, CH$_2$CH$_2$N), 3.42 (m, 1H, CH$_a$CHO), 3.64 (m, 4H, ArCH$_2$N), 3.69 (m, 1H, CH$_b$NO), 3.88 (t, 4H, CH$_2$CH$_2$N), 4.55 (m, 1H, CH$_2$CHO), 6.91 (m, 1H, ArH), 7.01 (m, 1H, ArH), 7.23-7.34 (m, 11H, ArH).

HPLC: 95.3%.

Example 13

Preparation of (S)-5-((dibenzylamino)methyl)-3-(3-(3-fluoro-4-morpholinophenyl)oxazolidin-2-one (Compound 4)

N-carbobenzoxy-3-fluoro-4-morpholinylaniline (0.33 g, 1 mmol) was added under nitrogen atmosphere to 8 mL of tetrahydrofuran under the protection of nitrogen flow. The solution was cooled to −30° C. and then the 2.5M solution of butyl lithium in tetrahydrofuran (1 mL, 2.5 mmol) was added and the mixture was stirred at −30° C.~−20° C. for 2 hours. (S)-1-chloro-3-(dibenzylamino)propan-2-ol (0.32 g, 1.1 mmol) was added and the reaction mixture was heated to 60° C. for 2 hours. After the solution was cooled down, saturated ammonium chloride solution and ethyl acetate were added to separate. The organic layer was washed with water and dried over anhydrous magnesium sulfate, filtered, and the solvent was evaporated to provide 0.32 g of white solid in 67% yield.

$^1$H NMR (300 MHz, CDCl$_3$) δ: 2.83 (m, 2H, CHCH$_2$N), 3.06 (t, 4H, CH$_2$CH$_2$N), 3.42 (m, 1H, CH$_a$CHO), 3.64 (m, 4H, ArCH$_2$N), 3.69 (m, 1H, CH$_b$NO), 3.88 (t, 4H, CH$_2$CH$_2$N), 4.55 (m, 1H, CH$_2$CHO), 6.91 (m, 1H, ArH), 7.01 (m, 1H, ArH), 7.23-7.34 (m, 11H, ArH).

HPLC: 96.2%.

Example 14

Preparation of (S)-5-(aminomethyl)-3-(3-fluoro-4-morpholinophenyl) oxazolidin-2-one (Compound 5)

(S)-5-((dibenzylamino)methyl)-3-(3-fluoro-4-morpholinophenyl)oxazolidin-2-one (0.95 g, 2 mmol) and 0.5 g of 10 wt % Pd—C were added to 20 mL acetone and the air was replaced with N$_2$. The reaction stirred under 5 Mpa hydrogen at room temperature (25° C.) for 5 hours. Filtered and the solvent was evaporated to provide 0.55 g of white solid in 93% yield.

$^1$H NMR (300 MHz, CDCl$_3$) δ: 3.02 (m, 6H, CHCH$_2$ N, CH$_2$NH$_2$), 3.76 (m, 1H, CH$_a$CHO), 3.84 (t, 4H, CHCH$_2$ N), 3.98 (m, 1H, CH$_b$NO), 4.65 (m, 1H, CHCH O), 6.90 (t, 1H, ArH), 7.12 (dd, 1H, ArH), 7.46 (dd, 1H, ArH).

HPLC: 99.2%.

Example 15

Preparation of (S)-5-(aminomethyl)-3-(3-fluoro-4-morpholinophenyl) oxazolidin-2-one (Compound 5)

(S)-5-((dibenzylamino)methyl)-3-(3-fluoro-4-morpholinophenyl)oxazolidin-2-one (0.95 g, 2 mmol) and 0.5 g of 10 wt % Pd—C were added to 20 mL ethyl acetate and the air was replaced with N$_2$. Hydrogen was passed into the mixture and the mixture was heated to 50° C. and reacted for 20 hours. Filtered and the solvent was evaporated to provide 0.53 g of white solid in 90% yield.

$^1$H NMR (300 MHz, CDCl$_3$) δ: 3.02 (m, 6H, CH$\underline{C}$H$_2$ N, CH$_2$N$\underline{H}_2$), 3.76 (m, 1H, C$\underline{H}_a$CHO), 3.84 (t, 4H, CH$\underline{CH_2}$ N), 3.98 (m, 1H, C$\underline{H}_b$NO), 4.65 (m, 1H, CH$\underline{C}$H O), 6.90 (t, 1H, ArH), 7.12 (dd, 1H, ArH), 7.46 (dd, 1H, ArH).
HPLC: 99.0%.

Example 16

Preparation of (S)-5-(aminomethyl)-3-(3-fluoro-4-morpholinophenyl) oxazolidin-2-one (Compound 5)

(S)-5-((dibenzylamino)methyl)-3-(3-fluoro-4-morpholinophenyl)oxazolidin-2-one (0.95 g, 2 mmol), 0.5 g 10 wt % Pd—C and ammonium formate (1.3 g, 20 mmol) were added to 20 mL acetone and the air was replaced with N$_2$. The mixture was heated to reflux and stirred for 10 hours. The mixture was filtered and separated by water. The organic layer was washed with brine, dried over anhydrous magnesium sulfate, filtered, and the solvent evaporated to provide 0.52 g of white solid in 88% yield.
$^1$H NMR (300 MHz, CDCl$_3$) δ: 3.02 (m, 6H, CH$\underline{C}$H$_2$ N, CH$_2$N$\underline{H}_2$), 3.76 (m, 1H, C$\underline{H}_a$CHO), 3.84 (t, 41H, CH$\underline{CH_2}$ N), 3.98 (m, 1H, C$\underline{H}_b$NO), 4.65 (m, 1H, CH$\underline{C}$H O), 6.90 (t, 1H, ArH), 7.12 (dd, 1H, ArH), 7.46 (dd, 1H, ArH).
HPLC: 98.9%.

Example 17

Preparation of Linezolid (Compound 1)

(S)-5-(aminomethyl)-3-(3-fluoro-4-morpholinophenyl) oxazolidin-2-one (0.3 g, 1 mmol), acetic anhydride (0.12 g, 1.2 mmol) and triethylamine (0.5 g, 5 mmol) were added to 10 mL ethyl acetate and the reaction mixture was stirred at room temperature for 2 hours. The organic layer was washed with brine, dried over anhydrous magnesium sulfate, filtered, most part of the solvent was evaporated, frozen crystallized and filtered to yield the crude product. The crude product was recrystallized with ethyl acetate to provide 0.30 g of linezolid in 88% yield.
$^1$H NMR (300 MHz, CDCl$_3$) δ: 2.02 (s, 3H, C$\underline{H}_3$CO), 3.05 (t, 4H, CH$\underline{C}$H$_2$ N), 3.75 (m, 1H, C$\underline{H}_a$CHO), 3.67 (m, 2H, CH$_2$NHCO), 3.87 (m, 4H, ArC$\underline{H}_2$N), 4.02 (m, 1H, CHbNO), 4.76 (m, 1H, CH$_2$CHO), 6.12 (t, 1H, NHCO), 6.93 (t, 1H, Ar H), 7.18 (dd, 1H, ArH), 7.46 (dd, ArH).
HPLC: 99.8%.

Example 18

Preparation of Linezolid (Compound 1)

(S)-5-((dibenzylamino)methyl)-3-(3-fluoro-4-morpholinophenyl)oxazolidin-2-one (0.95 g, 2 mmol) and 0.1 g 10 wt % Pd—C were added to 20 mL acetone and the air was replaced with N$_2$. The reaction went on under 5 Mpa hydrogen at room temperature for 5 hours. After filtered, acetic anhydrid (0.24 g, 2.4 mmol) and triethylamine (2.0 g, 20 mmol) were added and reacted for 2 hours at room temperature. The organic layer was washed with brine, dried over anhydrous magnesium sulfate, filtered, most part of the solvent was evaporated, frozen crystallized and filtered to provide the crude product. The crude product was recrystallized with ethyl acetate to provide 0.51 g of linezolid in 75% yield.
$^1$H NMR (300 MHz, CDCl$_3$) δ: 2.02 (s, 3H, C$\underline{H}_3$CO), 3.05 (t, 4H, CH$\underline{C}$H$_2$ N), 3.75 (m, 1H, C$\underline{H}_a$CHO), 3.67 (m, 2H, CH$_2$NHCO), 3.87 (m, 4H, ArC$\underline{H}_2$N), 4.02 (m, 1H, C$\underline{H}_b$NO), 4.76 (m, 1H, CH$\underline{C}$H O), 6.12 (t, 1H, NHCO), 6.93 (t, 1H, Ar H), 7.18 (dd, 1H, ArH), 7.46 (dd, 1H, ArH).
HPLC: 99.7%.

Example 19

Preparation of (S)-1-chloro-3-(dibenzylamino)propan-2-ol (Compound 2)

Dibenzylamine (39.4 g, 0.20 mol) and lithium hydroxide (48 mg, 2 mmol) were added to 100 mL N,N-dimethyl formamide. The mixture was stirred at 25° C. for 30 minutes. (S)-epichlorohydrin (18.6 g, 0.2 mol) was then added and the mixture was stirred at 0° C. for 8 hours. The mixture was filtered and the solvent was evaporated to provide 52 g colorless oil with 90% yield. HPLC: 99.0%.

Example 20

Preparation of (S)-1-chloro-3-(dibenzylamino)propan-2-ol (Compound 2)

Dibenzylamine (39.4 g, 0.20 mol) and zinc chloride (81.6 g, 0.6 mol) were added to 200 mL dimethyl sulfoxide. The mixture was stirred at 25° C. for 30 minutes. (S)-epichlorohydrin (37.2 g, 0.4 mol) was then added and reacted at 120° C. for 8 hours. The mixture was filtered and water was added to the filtrate. The filtrate was extracted with ethyl acetate for 3 times, and then the organic phases were combined, the solvent was evaporated to provide 53 g of colorless oil with 92% yield. HPLC: 99.0%.

Example 21

Preparation of (S)-1-chloro-3-(dibenzylamino)propan-2-ol (Compound 2)

Dibenzylamine (39.4 g, 0.20 mol) and stannic chloride (78.3 g. 0.30 mol) were added to 100 mL of acetone. The mixture was stirred at 25° C. for 30 minutes. (S)-epichlorohydrin (18.6 g, 0.2 mol) was then added and stirred at 60° C. for 8 hours. The mixture was filtered and the solvent was evaporated to provide 55 g of colorless oil with 94% yield. HPLC: 99.2%.

Example 22

Preparation of (S)-1-chloro-3-(dibenzylamino)propan-2-ol (Compound 2)

Dibenzylamine (39.4 g, 0.20 mol) and lithium chloride (12.6 g, 0.30 mol) were added to 100 mL of toluene. The mixture was stirred at 25° C. for 30 minutes. (S)-epichlorohydrin (18.6 g, 0.2 mol) was then added and stirred at 60° C. for 8 hours. The mixture was filtered and the solvent was evaporated to provide 52 g of colorless oil in 90% yield. HPLC: 99.3%.

Example 23

Preparation of (S)-1-chloro-3-(dibenzylamino)propan-2-ol (Compound 2)

Dibenzylamine (39.4 g, 0.20 mol) and ferric chloride (12.6 g. 0.30 mol) were added to 100 mL of ether. The mixture was stirred at 25° C. for 30 minutes, (S)-epichlorohydrin (18.6 g, 0.2 mol) was then added and stirred for at 60° C. 8 hours.

Filtered and the solvent was evaporated to provide 53 g of colorless oil in 92% yield. HPLC: 99%.

Example 24

Preparation of (S)-1-chloro-3-(dibenzylamino)propan-2-ol (Compound 2)

Dibenzylamine (39.4 g, 0.20 mol) and ferric chloride (12.6 g. 0.30 mol) were added to 100 mL of acetonitrile. The mixture was stirred at 25° C. for 30 minutes. (S)-epichlorohydrin (18.6 g, 0.2 mol) was then added and stirred at 60° C. for 8 hours. Filtered and the solvent was evaporated to provide 55 g of colorless oil in 94% yield. HPLC: 98%.

Example 25

Preparation of (S)-5-((dibenzylamino)methyl)-3-(3-fluoro-4-morpholinophenyl)oxazolidin-2-one (Compound 4)

N-carbobenzoxy-3-fluoro-4-morpholinylaniline (0.33 g, 1 mmol) was added to 8 mL of methanol. The solution was cooled to −30° C. under the protection of nitrogen flow and then the methanol solution containing 1 mmol of tert-butyl lithium was added. The mixture was stirred at −78° C.~−20° C. for 2 hours. (S)-1-chloro-3-(dibenzylamino)propan-2-ol (0.29 g, 1 mmol) was added and then the mixture was heated slowly to 100° C. and stirred for 2 hours. After the solution was cooled down, saturated ammonium chloride solution and ethyl acetate were added to separate. The organic layer was washed with water and dried over anhydrous magnesium sulfate, filtered, and evaporated to dryness to provide 0.31 g of white solid in 65% yield. HPLC: 99.2%.

Example 26

Preparation of (S)-5-((dibenzylamino)methyl)-3-(3-fluoro-4-morpholinophenyl)oxazolidin-2-one (Compound 4)

N-carbobenzoxy-3-fluoro-4-morpholinylaniline (0.33 g, 1 mmol) was added to 8 mL of acetone. The solution was cooled to −30° C. under the protection of nitrogen flow and then 50 mmol of lithium tert-butoxide was added. The mixture was stirred at −30° C.~−20° C. for 2 hours, (S)-1-chloro-3-(dibenzylamino)propan-2-ol (2.9 g, 10 mmol) was added and then the solution was heated slowly to 60° C. and stirred for 2 hours. After the solution was cooled down, saturated ammonium chloride solution and ethyl acetate were added to separate. The organic layer was washed with water and dried over anhydrous magnesium sulfate, filtered, and evaporated to dryness to provide 285 mg of white solid in 60% yield. HPLC: 99.2%.

Example 27

Preparation of (S)-5-((dibenzylamino)methyl)-3-(3-fluoro-4-morpholinophenyl)oxazolidin-2-one (Compound 4)

N-carbobenzoxy-3-fluoro-4-morpholinylaniline (0.33 g, 1 mmol) was added to 8 mL of toluene. The solution was cooled to −30° C. under the protection of nitrogen flow and then 50 mmol of lithium tert-butoxide was added. The mixture was stirred at −30° C.~−20° C. for 2 hours. (S)-1-chloro-3-(dibenzylamino)propan-2-ol (1.45 g, 5 mmol) was added and then the solution was heated slowly to 60° C. and stirred for 2 hours. After the solution was cooled down, saturated ammonium chloride solution and ethyl acetate were added to separate. The organic layer was washed with water and dried over anhydrous magnesium sulfate, filtered, and evaporated to dryness to provide 285 mg of white solid in 60% yield. HPLC: 99.2%.

Example 28

Preparation of (S)-5-((dibenzylamino)methyl)-3-(3-fluoro-4-morpholinophenyl)oxazolidin-2-one (Compound 4)

N-carbobenzoxy-3-fluoro-4-morpholinylaniline (0.33 g, 1 mmol) was added to 8 mL of dimethyl sulfoxide. The solution was cooled to −30° C. under the protection of nitrogen flow and then 50 mmol of lithium tert-butoxide was added. The mixture was stirred at −30° C.~−20° C. for 2 hours. (S)-1-chloro-3-(dibenzylamino)propan-2-ol (1.45 g, 5 mmol) was added and then the solution was heated slowly to 60° C. and stirred for 2 hours. After the solution was cooled down, saturated ammonium chloride solution and ethyl acetate were added to separate. The organic layer was washed with water and dried over anhydrous magnesium sulfate, filtered, and evaporated to dryness to provide 280 mg white solid with 59% yield. HPLC: 99.2%.

Example 29

Preparation of (S)-5-((dibenzylamino)methyl)-3-(3-fluoro-4-morpholinophenyl)oxazolidin-2-one (Compound 4)

N-carbobenzoxy-3-fluoro-4-morpholinylaniline (0.33 g, 1 mmol) was added to 8 mL acetonitrile. The solution was cooled to −30° C. under the protection of nitrogen flow and then 50 mmol lithium tert-butoxide was added. The mixture reacted at −30° C.~−20° C. for 2 hours. (S)-1-chloro-3-(dibenzylamino)propan-2-ol (1.45 g, 5 mmol) was added and then the solution was heated slowly to 60° C. and the reaction was maintained for 2 hours. After the solution was cooled down, saturated ammonium chloride solution and ethyl acetate were added to separate. The organic layer was washed with water and dried over anhydrous magnesium sulfate, filtered, and evaporated to dryness to provide 285 mg of white solid in 60% yield. HPLC: 99.2%.

Example 30

Preparation of (S)-5-(aminomethyl)-3-(3-fluoro-4-morpholinophenyl) oxazolidin-2-one (Compound 5)

Compound 4 (0.95 g, 2 mmol) and 10% Pd—C (0.02 mmol) were added to 20 mL of methyl alcohol and the air was replaced with $N_2$. Hydrazine hydrate (4 mmol) was added and on the mixture was stirred at 0° C. for 24 hours. Water was added and the mixture was extracted with ethyl acetate. The organic layer was washed with brine, dried over anhydrous magnesium sulfate, filtered, and the solvent was evaporated to provide 0.52 g of white solid in 88% yield. HPLC: 99%.

Example 31

Preparation of (S)-5-(aminomethyl)-3-(3-fluoro-4-morpholinophenyl) oxazolidin-2-one (Compound 5)

Compound 4 (0.95 g, 2 mmol) and 10% Pd—C (0.02 mmol) were added to 20 mL of ether and the air was replaced with N₂. Formic acid (94 mg, 2 mmol) was added and the mixture was stirred at 80° C. for 2 hours, Water was added and the mixture was extracted with ethyl acetate. The organic layer was washed with brine, dried over anhydrous magnesium sulfate, filtered, and the solvent was evaporated to provide 0.46 g of white solid in 78% yield. HPLC: 99.2%.

Example 32

Preparation of (S)-5-(aminomethyl)-3-(3-fluoro-4-morpholinophenyl) oxazolidin-2-one (Compound 5)

Compound 4 (0.95 g, 2 mmol) and 10% Pd—C (1 mmol) were added to the mixture of 20 mL of ethanol and 2 mL of water and the air was replaced with N₂. The triethylamine-Formic acid azeotrope (704 mg, 4 mmol) was added and the mixture was stirred at 80° C. for 12 hours. Water was added and the mixture was extracted with ethyl acetate. The organic layer was washed with brine, dried over anhydrous magnesium sulfate, filtered, and the solvent was evaporated to provide 0.49 g of white solid in 84% yield. HPLC: 99.3%.

Example 33

Preparation of (S)-5-(aminomethyl)-3-(3-fluoro-4-morpholinophenyl) oxazolidin-2-one (Compound 5)

(S)-5-((dibenzylamino)methyl)-3-(3-fluoro-4-morpholinylphenyl)-2-oxo-oxazoline (0.95 g, 2 mmol) and 10 wt % Pd—C (0.5 g) were added to 20 mL of toluene and the air was replaced with N₂ and the reaction mixture was stirred under 25 atm hydrogen for 5 hours at room temperature (25° C.). The mixture was filtered and the solvent was evaporated to provide 0.55 g of white solid in 93% yield. HPLC: 99%.

Example 34

Preparation of (S)-5-(aminomethyl)-3-(3-fluoro-4-morpholinophenyl) oxazolidin-2-one acetate (the acetate of Compound 5)

(S)-5-((dibenzylamino)methyl)-3-(3-fluoro-4-morpholinophenyl)oxazolidin-2-one (9.5 g, 20 mmol) and 1 g of 10 wt % Pd—C were added to 50 mL of ethyl acetate and the air was replaced with N₂. Hydrogen was passed into the mixture and then the mixture was heated to 50° C. and stirred for 20 hours. The mixture was filtered and acetic acid (1.4 g, 24 mmol) was added dropwise into the filtrate. After cooled to 0° C., the solution was filtered and washed with ethyl acetate to provide 6.31 g of white solid in 89% yield.

$^1$H NMR (300 MHz, d-DMSO) δ: 2.05 (s, 3H, HOAc), 2.88 (m, 6H, CH$_2$CH$_2$N, CH$_2$NH$_2$), 3.78 (m, 1H, CH$_a$CHO), 3.91 (t, 4H, CH$\underline{C}$H$_2$ N), 3.99 (m, 1H, CH$_b$NO), 4.71 (m, 1H, CH$\underline{C}$H O), 6.880 (t, 1H, ArH), 7.16 (dd, 1H, ArH), 7.50 (dd, 1H, ArH).

HPLC: 99.5%.

Example 35

Preparation of Linezolid (Compound 1)

(S)-5-(aminomethyl)-3-(3-fluoro-4-morpholinophenyl) oxazolidin-2-one acetate (3.5 g, 10 mmol) was dissolved in 20 mL of water. The solution was heated to 50° C. and then acetic anhydride (0.72 g, 12 mmol) was added dropwise and stirred at 50° C. for 2 hours. The mixture was cooled down to 0° C. to crystallize, filtered, washed with water, dried and recrystallized with ethyl acetate to provide 3.0 g of Linezolid in 88% yield.

$^1$H NMR (300 MHz, CDCl$_3$) δ: 2.02 (s, 3H, CH$_3$CO), 3.05 (t, 4H, CH$\underline{C}$H$_2$ N), 3.75 (m, 1H, CH$_a$CHO), 3.67 (m, 2H, CH$_2$NHCO), 3.87 (m, 4H, ArCH$_2$N), 4.02 (m, 1H, CH$_b$NO), 4.76 (m, 1H, CH$_2$CHO), 6.12 (t, 1H, NHCO), 6.93 (t, 1H, Ar H), 7.18 (dd, 1H, ArH), 7.46 (dd, 1H, ArH).

HPLC: 99.9%.

Example 34

Preparation of (S)-5-(aminomethyl)-3-(3-fluoro-4-morpholinophenyl) oxazolidin-2-one acetate (the acetate of Compound 5)

(S)-5-((dibenzylamino)methyl)-3-(3-fluoro-4-morpholinophenyl)oxazolidin-2-one (0.95 g, 2 mmol) and 10 wt % Pd—C (0.01 mmol) were added to 20 mL of ethanol and the air was replaced with N₂. Hydrogen was passed into the mixture and then the mixture was heated to 50° C. and stirred for 20 hours. The mixture was filtered and acetic acid (2.4 mmol) was added dropwise into the filtrate. After cooled to 0° C., the mixture was filtered and washed with ethyl acetate to provide the white solid in 88% yield.

HPLC: 99.5%.

Example 35

Preparation of (S)-5-(aminomethyl)-3-(3-fluoro-4-morpholinophenyl) oxazolidin-2-one acetate (the acetate of Compound 5)

Compound 4 (0.95 g, 2 mmol) and 10 wt % Pd—C (0.02 mmol) were added to 20 mL of methylene dichloride and the air was replaced with N₂. Hydrazine hydrate (4 mmol) was added and the reaction mixture was stirred at 0° C. for 24 hours. Water was added and the solution was extracted with ethyl acetate. The organic layer was washed with brine, dried over anhydrous magnesium sulfate, and filtered. Acetic acid (2.4 mmol) was added dropwise into the filtrate. After cooled to 0° C., the mixture was filtered and washed with ethyl acetate to provide a white solid in 87% yield. HPLC: 99%.

Example 36

Preparation of (S)-5-(aminomethyl)-3-(3-fluoro-4-morpholinophenyl) oxazolidin-2-one (the acetate of Compound 5)

(S)-5-((dibenzylamino)methyl)-3-(3-fluoro-4-morpholinophenyl)oxazolidin-2-one (0.95 g, 2 mmol), 10 wt % Pd—C (1 mmol) and ammonium formate (1.3 g, 20 mmol) were added to 20 mL of dioxane and the air was replaced with N₂. The system was heated to reflux and reaction mixture was stirred for 10 hours. The mixture was filtered and water was added to separate. The organic layer was washed with brine, dried over anhydrous magnesium sulfate, and filtered. Acetic acid (2.4 mmol) was added dropwise into the filtrate. After cooled to 0° C., the solution was filtered and washed with ethyl acetate to provide a white solid in 87% yield. HPLC: 99%.

Example 37

Preparation of (S)-5-(aminomethyl)-3-(3-fluoro-4-morpholinophenyl) oxazolidin-2-one acetate (the acetate of Compound 5)

Compound 4 (0.95 g, 2 mmol) and 10% Pd—C (0.02 mmol) were added to 20 mL of toluene and the air was replaced with $N_2$. Formic acid (94 mg, 2 mmol) was added and the reaction mixture was stirred at 80° C. for 2 hours Water was added to stratify and the mixture was extracted with ethyl acetate. The organic layer was washed with brine, dried over anhydrous magnesium sulfate and filtered. Acetic acid (2.4 mmol) was added dropwise in the filtrate. After cooled to 0° C., the mixture was filtered and washed with ethyl acetate to provide a white solid in 86% yield. HPLC: 99%.

Example 38

Preparation of (S)-5-(aminomethyl)-3-(3-fluoro-4-morpholinophenyl) oxazolidin-2-one acetate (the acetate of Compound 5)

Compound 4 (0.95 g, 2 mmol) and 10% Pd—C (1 mmol) were added to the mixture of 20 mL of methanol and 2 mL of water and the air was replaced with $N_2$. The triethylamine-formic acid azeotrope (704 mg, 4 mmol) was added to the mixture and reaction mixture was stirred at 80° C. for 12 hours, Water was added to separate and the mixture was extracted with ethyl acetate. The organic layer was washed with brine, dried over anhydrous magnesium sulfate and filtered. Acetic acid (2.4 mmol) was added dropwise into the filtrate. After cooled to 0° C., the mixture was filtered and washed with ethyl acetate to provide a white solid in 86.5% yield. HPLC: 99.1%.

Example 39

Preparation of (S)-5-(aminomethyl)-3-(3-fluoro-4-morpholinophenyl) oxazolidin-2-one acetate (the acetate of Compound 5)

Compound 4 (0.95 g, 2 mmol) was added to 10 mL of methylene dichloride and the solution was cooled to −10° C. The methylene dichloride solution of boron tribromide (2 ml, 2 mmol) was added dropwise into the solution under the protection of $N_2$. The reaction mixture was stirred at −10° C. for 3 hours and then warmed slowly up to room temperature and continued for 2 hours. The reaction mixture was poured into ice water and the organic layer was separated. The aqueous layer was extracted with 5 mL of methylene dichloride and the organic layers were combined. The organic layer was washed with brine, dried over anhydrous magnesium sulfate and filtered. Acetic acid (2.4 mmol) was added dropwise into the filtrate. After cooled to 0° C., the mixture was filtered and washed with ethyl acetate to provide a white solid in 90% yield. HPLC: 99.0%.

Example 40

Preparation of (S)-5-(amino methyl)-3-(3-fluoro-4-morpholinylphenyl)-2-oxo-oxazoline acetate (the acetate of Compound 5)

Compound 4 (0.95 g, 2 mmol) was added to 10 mL methylene dichloride and the solution was cooled to 0° C. The methylene dichloride solution of boron trifluoride (2 ml, 2 mmol) was added dropwise into the solution under the protection of $N_2$. The reaction mixture was stirred at 0° C. for 3 hours and then warmed slowly up to reflux and continued for 5 hours. The reaction mixture was poured into ice water and the organic layer was separated. The aqueous portion was extracted with 5 mL methylene dichloride and the organic layers were combined. The organic layer was washed with brine, dried over anhydrous magnesium sulfate and filtered. Acetic acid (2.4 mmol) was added dropwise into the filtrate. After cooled to 0° C., the mixture was filtered and washed with ethyl acetate to provide a white solid in 88% yield. HPLC: 98.3%.

The invention claimed is:

1. A method for preparing a linezolid of Compound 1 comprising,
    (1) preparing a Compound 5 or an acetic acid salt thereof by debenzylation of a Compound 4 in a solvent;
    (2) preparing the linezolid of Compound 1 by an acetylation reaction of the amino group of the Compound 5 or the acetic acid salt thereof obtained in step (1) in a solvent;

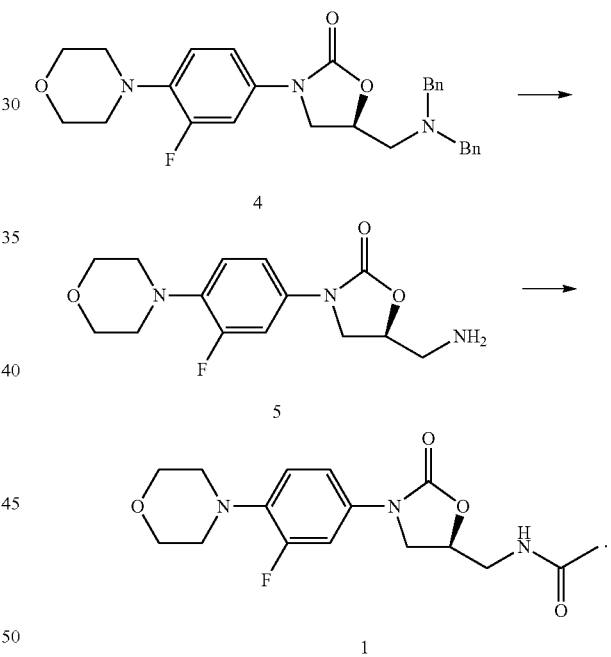

2. The method according to claim 1, wherein, in step (1), the Compound 5 is obtained by the following method:
    debenzylating the Compound 4 in an inert organic solvent in presence of a catalyst and a hydrogen source to yield Compound 5.
3. The method according to claim 2, wherein:
    the catalyst is Pd—C and/or Pt—C;
    a dosage of the catalyst is 0.01 to 0.5 times of a molar quantity of Compound 4;
    the hydrogen source is selected from the group consisting of hydrogen, hydrazine hydrate, ammonium formate, formic acid, triethylamine-formic acid azeotrope, and mixtures thereof;
    a dosage of the hydrogen source is more than the molar quantity of the Compound 4;

the inert organic solvent is selected from the group consisting of lower alcohol, ketone solvent, ester solvent, aromatic hydrocarbon, ether, and mixtures thereof;
a reaction temperature is 0° C. to 50° C.;
a reaction pressure is 1 to 50 atm;
a reaction time is detected until an end of the reaction.

4. The method according to claim 1, wherein, the acetic acid salt of the Compound 5 is prepared by
(1) debenzylating Compound 4 in presence of a catalyst and a hydrogen source in an organic solvent and/or water, and then
(2) forming a salt by reacting the Compound 5 with acetic acid wherein, the catalyst is selected from the group consisting of Pd—C, Pt—C, boron tribromide, boron triflouride, and mixtures thereof;
a molar ratio of the catalyst to the Compound 4 is 0.005 to 0.5;
the hydrogen source is selected from the group consisting of hydrogen, hydrazine hydrate, ammonium formate, formic acid, triethylamine-formic acid azeotrope, and mixtures thereof;
a dosage of the hydrogen source is more than the molar quantity of Compound 4;
the organic solvent is selected from the group consisting of ethyl acetate, ethanol, toluene, dioxane, methylene dichloride, and mixtures thereof;
a reaction time is detected until an end of the reaction;
a reaction temperature is 0° C. to 100° C.

5. The method according to claim 1, wherein:
the Compound 4 is obtained by
performing a cyclization reaction in solvent with Compound 2 and Compound 3;

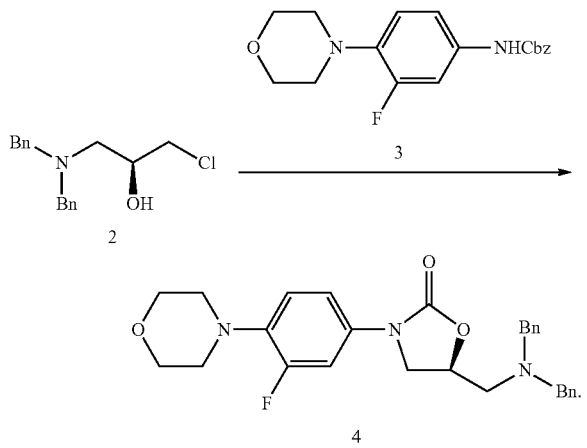

6. The method according to claim 5, wherein:
the Compound 4 is obtained by the following method:
performing a cyclization reaction of Compound 2 and Compound 3 in an inert organic solvent in presence of an alkali.

7. The method according to claim 6, wherein:
a dosage of the Compound 2 is 1 to 10 times of a molar quantity of Compound 3;
the alkali is selected from the group consisting of n-butyl lithium, tert-butyl lithium, lithium hydroxide, lithium tert-butoxide, and mixtures thereof;
a dosage of the alkali is 1 to 10 times of a molar quantity of the Compound 2;
the inert organic solvent is selected from the group consisting of lower alcohol, ketone, aromatic hydrocarbon, ether, haloalkane, N,N-dimethyl formamide, N,N-dimethyl acetamide, dimethyl sulfoxide and acetonitrile;
a reaction temperature is −78° C. to 100 C;
a reaction time is detected until an end of the reaction.

8. The method according to claim 5, wherein:
the Compound 2 is obtained by
(1) performing a nucleophilic ring opening reaction in either
(i) a solvent, or
(ii) without a solvent wherein a nucleophilic ring opening reaction is performed by (S)-epichlorohydrin and dibenzyl amine;

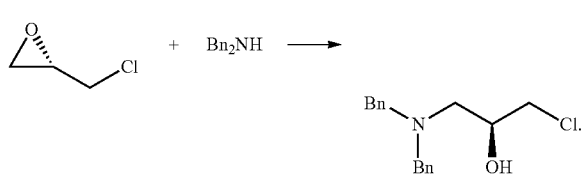

9. The method according to claim 8, wherein the Compound 2 is obtained by a nucleophilic ring opening reaction of (S)-epichlorohydrin and dibenzyl amine in presence of Lewis acid.

10. The method according to claim 9, wherein the Lewis acid is selected from the group consisting of lithium chloride, lithium bromide, calcium chloride, lithium hydroxide, zinc chloride, stannic chloride, ferric chloride, and mixtures thereof;
a dosage of the Lewis acid is 0.01 to 3 times of a molar quantity of dibenzyl amine;
a dosage of (S)-epichlorohydrin is more than the molar quantity of dibenzyl amine;
the inert organic solvent is selected from the group consisting of lower alcohol, ketone, ester, aromatic hydrocarbon, ether, haloalkane, N,N-dimethyl formamide, N,N-dimethyl acetamide, dimethyl sulfoxide, acetonitrile, and mixtures thereof;
a reaction temperature is 0° C. to 120° C.; and
a reaction time is detected until an end of the reaction.

* * * * *